United States Patent [19]

Lind et al.

[11] 4,034,006

[45] July 5, 1977

[54] PROCESS FOR THE MANUFACTURE OF ALKALI SALTS OF 3,5-DISUBSTITUTED 4-HYDROXYBENZOIC ACIDS AND THEIR FREE ACIDS

[75] Inventors: Hanns Lind, Liestal; Jean Rody, Basel; Heimo Brunnetti, Reinach, all of Switzerland

[73] Assignee: Ciba-Geigy Corporation, Ardsley, N.Y.

[22] Filed: Feb. 24, 1975

[21] Appl. No.: 552,527

Related U.S. Application Data

[63] Continuation of Ser. No. 282,638, Aug. 21, 1972, abandoned.

[30] Foreign Application Priority Data

Sept. 28, 1971 Switzerland .................. 14105/71

[52] U.S. Cl. ................... 260/521 C; 260/520 A; 260/473 R; 260/439 R
[51] Int. Cl.$^2$ ....................................... C07C 51/15
[58] Field of Search ................. 260/521 C, 520 A

[56] References Cited

UNITED STATES PATENTS

| | | | |
|---|---|---|---|
| 2,807,643 | 9/1957 | Hartley | 260/521 C |
| 3,532,745 | 10/1970 | Hirao | 260/521 C |
| 3,825,593 | 7/1974 | Meek | 260/521 C |

*Primary Examiner*—Norman Morgenstern
*Attorney, Agent, or Firm*—Charles W. Vanecek; Nestor W. Shust

[57] ABSTRACT

A new process for the preparation of alkalimetal salts of 3,5-substituted 4-hydroxybenzoic acids and the free acids thereof, which comprises reacting a 2,6-disubstituted phenol in a mixture of water and a dipolar aprotic solvent with an alkalimetal hydroxide, removing the water, treating the reaction mixture with carbon dioxide and in case of preparing the free acids treating the reaction mixture with a mineral acid.

The alkalimetal salts of 4-hydroxybenzoic acids and the free acids thereof are compounds which can be used as intermediates for stabilizers.

6 Claims, No Drawings

PROCESS FOR THE MANUFACTURE OF ALKALI SALTS OF 3,5-DISUBSTITUTED 4-HYDROXYBENZOIC ACIDS AND THEIR FREE ACIDS

This is a continuation of application Ser. No. 282,638 filed on Aug. 12, 1972, now abandoned.

The present invention relates to a new process for the manufacture of alkali salts of 3,5-disubstituted 4-hydroxybenzoic acids, especially 3,5-dialkyl-4-hydroxybenzoic acids, and their free acids.

The best-known manufacturing process for p-hydroxybenzoic acids is the Kolbe-Schmitt reaction in which the corresponding potassium phenolate is treated with gaseous carbon dioxide under pressure. Recently, attempts have been made to avoid the disadvantages of this heterogeneous gal-solid reaction by carrying out the reaction in a homogeneous phase.

For this purpose, separately manufactured and carefully dried alkali metal phenolates were carboxylated in dipolar aprotic solvents with carbon dioxide gas. However, using this process, sterically hindered 2,6-disubstituted phenols do not give any defined reaction products. Only when using special carboxylation reagents, for example magnesium methyl-carbonate, did it become possible to manufacture the corresponding carboxylic acids in good yields even from sterically hindered phenols, such as 2,6-di-tert.-butyl phenol. It is a characteristic of this manufacturing process that it has to be carried out in absolutely anhydrous solvents with exclusion of water, which is why it was also not possible to use cheap alkali hydroxides as bases.

The present process according to the invention now makes it possible to avoid these disadvantages. It is characterised in that compounds of the general formula I

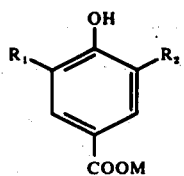

in which $R_1$ represents an alkyl radical with 1 to 5 carbon atoms or a cycloalkyl radical with 6 to 8 cabon atoms, $R_2$ represents an alkyl radical with 4 to 8 carbon atoms which is branched in the α-position or a cycloalkyl radical with 6 to 8 carbon atoms and M represents hydrogen or an alkali metal atom, can be manufactured by treating a phenol of the general formula II

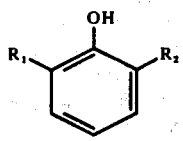

in which $R_1$ and $R_2$ have the meaning indicated under the formula I, in a mixture of water and a dipolar aprotic solvent, with an alkali metal hydroxide, reacting the reaction product, after removal of the water and without intermediate isolation, in the organic medium at elevated temperature, with carbon dioxide under normal pressure, and optionally liberating the acid from the alkali metal salf formed.

If $R_1$ represents an alkyl radical with 1 to 5 carbon atoms, methyl, ethyl, n-propyl, iso-propyl, n-butyl, sec.-butyl, tert.-butyl, iso-pentyl or tert.-pentyl radicals may, for example be involved. When denoting a cycloalkyl radical with 6 to 8 carbon atoms, $R_1$ is, for example, a cyclohexyl, methyl-cyclohexyl, cycloheptyl or cyclooctyl radical. Preferably, $R_1$ is an alkyl radical with 1 to 4 carbon atoms, especially the tert.-butyl radical.

If $R_2$ represents an alkyl radical with 4 to 8 carbon atoms which is branched in the α-position, sec.-butyl, tert.-butyl, tert.-pentyl, 1-methylpentyl or 1,1,3,3-tetra-methylbutyl radicals may, for example, be involved. If $R_2$ denotes a cycloalkyl radical with 6 to 8 carbon atoms, what has been stated for $R_1$ above applies. Preferably, $R_2$ is an alkyl radical with 4 to 5 carbon atoms which is branched in the α-position, for example the sec-butyl or the tert.-pentyl radical, but especially the tert.butyl radical.

When M denotes an alkali metal atom it is, for example, lithium, sodium or potassium; preferably, however, M preferably represents sodium.

As alkali metal hydroxides it is possible to use, for example, lithium hydroxide, sodium hydroxide or potassium hydroxide in the process according to the invention; sodium hydroxide is preferentially employed.

The class of the dipolar aprotic solvents is defined, for example, in A. J. Parker, Chemical Reviews, Vol. 69 (1969), page 2. Such solvents, which are stable under the reaction conditions, are used as a mixture with water in the process according to the invention. Examples are: dimethylformamide, dimethylacetamide, dimethylsulphoxide, hexamethylphosphoramide, N-methylpryrrolidone, tetramethylurea and sulpholane. A mixture of water and dimethylformamide is preferentially used.

The process according to the invention is appropriately carried out at temperatures of room temperature (approx. 20°C) to 95°C but particularly preferentially at temperatures of between 60° and 85°C. It is furthermore advantageous to carry out the reaction with exclusion of oxygen, for example in a nitrogen atmosphere.

The alkali metal hydroxide is advantageously used in equivalent amount. It can, for example, be added to the organic phase after prior solution in water, or can be dissolved in the aqueous organic solvent.

The water can be removed from the initial reaction mixture, consisting of alkali metal hydroxide, 2,6-disubstituted phenol, organic solvent and water by fractional distillation or, if the organic solvent used forms an azeotrope with water, by azeotropic distillation — in both cases optionally under reduced pressure. In order to facilitate the removal of water it is possible to add to the reaction mixture an "entraining agent" which permits rapid reduction of the water content through azeotrope formation. Such "entraining agents" are, for example, xylene, toluene or benzene.

The subsequent reaction of the reaction mixture with carbon dioxide is carried out conventionally, working at normal pressure and, appropriately, using an excess over the theoretically calculated amount of carbon dioxide. In general, the reaction is complete after adding approx. 2 mols of carbon dioxide per 1 mol of phenol of the general formula II.

The compounds of the general formula I are isolated from the reaction mixture in accordance with customary methods, for example by removing the organic solvent wholly or partially by distillation and replacing it by water. The alkali metal salt produced in the reaction with carbon dioxide can also be isolated as such and, for example, be used directly for further reactions. The corresponding free hydroxybenzoic acid can be precipitated by acidifying the aqueous solution of the alkali metal salt.

The 3,5-disubstituted 4-hydroxybenzoic acids which can be manufactured in accordance with the process of the invention, and the corresponding alkali metal salts, are intermediate products for the manufacture of corresponding alkyl, aryl and metal benzoates which, because of their excellent light protection in polyolefine substrates, represent important light protection agents.

The present invention for the first time makes it possible to manufacture 3,5-disubstituted 4-hydroxybenzoic acids, especially 3,5-dialkyl-4-hydroxybenzoic acids, under technically simple and therefore also commercially advantageous conditions: the expensive manufacture of pre-dried phenolates is eliminated. It is therefore possible to work in a one-pot process in site of using alkali metal hydroxides as bases; no special complex carboxylation reagents are required; the reaction times are short and the reaction temperatures are low. Nevertheless high yields (far above 50% of theory) are achieved and the end products are directly obtained in such a pure form that they can in general be used, without intermediate purification, for the manufacture of the desired light protection agent; hence expensive purification methods are eliminated for these also.

It is extremely surprising — and an explanation thereof is currently not available — that sterically hindered phenols can be carboxylated under the indicated conditions and that in this way the desired hydroxybenzoic acids can be obtained in good yields from the 2,6-disubstituted phenols according to the definition.

In the examples which follow, percentages (%) denote percentages by weight.

EXAMPLE 1

206 g (1 mol) of 2,6-di-tert.-butylphenol and 40 g (1 mol) of sodium hydroxide are dissolved in a mixture of 500 ml of dimethylformamide and 30 ml of water by stirring under nitrogen at room temperature. A mixture of dimethylformamide and water is distilled from this reaction solution at boiling point 30–50°C/approx. 20 mm Hg until the water content in the last sample of the distillate is approx. 0.5% (after approx. 300 to 350 ml of distillate). After releasing the vacuum with nitrogen, carbon dioxide gas is passed in with vigorous stirring, in the course of which the temperature rises to approx. 88°C. After 1½ hours, the gas supply is stopped at this temperature, nitrogen is introduced and the reaction mixture is treated with 400 ml of 1,2,4-trichlorobenzene. In the course thereof, the temperature drops to 50°C. Approx. 200 ml of dimethylformamide are now distilled off at boiling point 50°C/approx. 20 mm Hg, the residue — a suspension which can be stirred — is treated with approx. 500 ml of water under nitrogen until the reaction product has completely dissolved and, after separation of the phases, 196 g of 3,5-di-tert.-butyl-4-hydroxybenzoic acid (yield, 80% of theory) are precipitated from the aqueous solution by acidification with concentrated hydrochloric acid. The product is a colourless crystal powder of melting point 214°–215°C. After combining the dimethylformamide distillates and distilling under normal pressure, aprox. 480 ml of dimethylformamide are recovered.

The acid thus obtained was used, for example, for the manufacture of n-octadecyl-3,5-di-tert.-butyl-4-hydroxy-benzoate, with this product being obtained directly, without expensive purification operations, in a purity suitable for use.

EXAMPLES 2–5

If in Example 1, whilst otherwise using the same procedure, the 206 g of 2,6-di-tert.-butylphenol are replaced by equivalent amounts of the phenols indicated in the table below, the hydroxybenzoic acids characterised in Columns 4–6 are obtained after recrystallisation accoarding to Column 3 of the table.

Table

| Example No. | Phenol | recrystallised from | Hydroxybenzoic acid | Melting point | Yield % of theory |
|---|---|---|---|---|---|
| 2 | 2-tert.-butyl-6-methylphenol | glacial acetic acid/water | 3-tert.-butyl-5-methyl-4-hydroxybenzoic acid | 180–182° C | 75 |
| 3 | 2-tert.-butyl-6-cyclohexylphenol | toluene/ligroin | 3-tert.-butyl-5-cyclohexyl-4-hydroxybenzoic acid | 178–179° C | 71 |
| 4 | 2,6-di-sec.-butylphenol | benzene/n-hexane | 3,6-di-sec.-butyl-4-hydroxybenzoic acid | 109–110° C | 78 |
| 5 | 2,6-di-cyclooctylphenol | ligroin | 3,5-di-cyclooctyl-4-hydroxybenzoic acid | 185–186° C | 63 |

EXAMPLE 6

A mixture of dimethylformamide/water is distilled from a solution of 206 g (1 mol) of 2,6-di-tert.-butylphenol and 80 g of a 50% strength aqueous sodium hydroxide solution in 500 ml of dimethylformamide at boiling point 30°–50°C/approx. 20 mm Hg until the water content in the last sample of the distillate is approx. 1.5%. After releasing the vacuum with nitrogen, carbon dioxide gas is passed into the reaction solution, with vigorous stirring, in the course of which the temperature of the solution rises to approx 85°C. After 1½ hours at this temperature, the reaction mixture is cooled to 60°C and 450 ml of a 20% strength sodium chloride solution are added under carbon dioxide gas. The resulting clear reaction solution is thereafter cooled, whereupon crystallisation starts at room temperature and is completed by stirring for 0.5 hours at 0°–5°C. Filtration, successive washing with 200 ml of 20% strength sodium chloride solution and 200 ml of n-hexane and drying the crystals to constant weight in vacuo at 40°C yields colourless sodium 3,5-di-tert.-butyl-4-hydroxy-benzoate, containing water of crystallisation; when this substance is dissolved in 500 ml of water and precipitated with concentrated hydrochloric acid, it yields 189 g (yield, 77% of theory) of 3,5-di-tert.-butyl-4-hydroxybenzoic acid of melting point 215°C.

Aqueous solutions of sodium 3,5-di-tert.-butyl-4-hydroxybenzoate thus obtained were used, for example, for the manufacture of nickel 3,5-di-tert.-butyl-4-hydroxybenzoate, whereupon this product was directly obtained in a purity suitable for use.

We claim:

1. A process for the manufacture of compounds of the general formula I

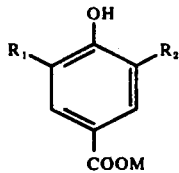

wherein $R_1$ and $R_2$ are both tert.-butyl, sec.-butyl or cycloocytl, or $R^1$ is tert.-butyl and $R_2$ is methyl or $R_1$ is tert.-butyl and $R_2$ is cyclohexyl, and M is hydrogen or an alkali metal atom, in which process a phenol of the general formula II

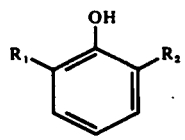

wherein $R_1$ and $R_2$ have the meaning indicated under the formula I, is treated, in a mixture of water and a dipolar aprotic solvent, with an alkali metal hydroxide and the reaction product, after removal of the water, is reacted, without intermediate isolation and in the organic medium, at elevated temperature, with carbon dioxide under normal pressure and the acid is optionally liberated from the resulting alkali metal salt.

2. A process according to claim 1 wherein M is hydrogen.

3. A process according to claim 1 wherein the starting material is a phenol of the general formula II in which $R_1$ and $R_2$ are tert.-butyl.

4. A process according to claim 1 wherein the mixture of water and a dipolar aprotic solvent which is used is a mixture of water and diemthylformamide.

5. A process according to claim 1 wherein the reaction is carried out at a temperature of 60° to 85°C.

6. A process according to claim 1 wherein the alkali metal hydroxide used is sodium hydroxide.

* * * * *